(12) United States Patent
Kwon et al.

(10) Patent No.: US 11,083,380 B2
(45) Date of Patent: Aug. 10, 2021

(54) BIO-SIGNAL ACQUIRING APPARATUS, BIO-SIGNAL ACQUIRING METHOD, AND BIO-INFORMATION ESTIMATING METHOD

(71) Applicant: SAMSUNG ELECTRONICS CO., LTD., Suwon-si (KR)

(72) Inventors: Yong Joo Kwon, Yongin-si (KR); Sang Yun Park, Hwaseong-si (KR); Jae Min Kang, Seoul (KR); Byung Hoon Ko, Hwaseong-si (KR); Jeong Eun Hwang, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 130 days.

(21) Appl. No.: 16/389,014

(22) Filed: Apr. 19, 2019

(65) Prior Publication Data
US 2020/0085320 A1    Mar. 19, 2020

(30) Foreign Application Priority Data
Sep. 18, 2018    (KR) ........................ 10-2018-0111200

(51) Int. Cl.
*A61B 5/0205*    (2006.01)
*G01L 5/00*    (2006.01)
(Continued)

(52) U.S. Cl.
CPC ............ *A61B 5/02055* (2013.01); *A61B 5/01* (2013.01); *A61B 5/0533* (2013.01); *A61B 5/0535* (2013.01); *A61B 5/1102* (2013.01); *A61B 5/1172* (2013.01); *A61B 5/25* (2021.01); *A61B 5/389* (2021.01); *A61B 5/6843* (2013.01); *A61B 5/70* (2013.01); *A61B 5/7278* (2013.01);
(Continued)

(58) Field of Classification Search
CPC . A61B 5/02055; A61B 5/1172; A61B 5/6843; A61B 5/0488; G01D 5/24
See application file for complete search history.

(56) References Cited

U.S. PATENT DOCUMENTS

| 8,764,655 B2 | 7/2014 | Yoo |
| 2011/0015504 A1 | 1/2011 | Yoo |

(Continued)

FOREIGN PATENT DOCUMENTS

| JP | 2017-148580 A | 8/2017 |
| KR | 10-2011-0080124 A | 7/2011 |

(Continued)

*Primary Examiner* — Brian T Gedeon
*Assistant Examiner* — Joshua Andrew Schum-Houck
(74) *Attorney, Agent, or Firm* — Sughrue Mion, PLLC

(57) ABSTRACT

A bio-signal acquiring apparatus includes a sensor part and a signal processor. The sensor part includes a bio-signal sensor, a load sensor, and an ultrasonic sensor array, the bio-signal sensor configured to detect a bio-signal of an object that comes into contact with the sensor part, the load sensor configured to detect a contact load of the object, and the ultrasonic sensor array configured to detect contact load distribution of the object. The signal processor is configured to obtain a contact load of the object at a region of interest based on the contact load and the contact load distribution, and configured to output the contact load of the object at the region of interest and the bio-signal.

19 Claims, 14 Drawing Sheets

(51) Int. Cl.
*A61B 5/1172* (2016.01)
*A61B 5/00* (2006.01)
*A61B 5/01* (2006.01)
*A61B 5/11* (2006.01)
*A61B 5/0533* (2021.01)
*A61B 5/0535* (2021.01)
*G01B 17/00* (2006.01)
*A61B 5/25* (2021.01)
*A61B 5/024* (2006.01)
*G01D 5/24* (2006.01)
*G01K 13/20* (2021.01)
*A61B 5/389* (2021.01)

(52) U.S. Cl.
CPC .............. *G01B 17/00* (2013.01); *G01D 5/24* (2013.01); *G01K 13/20* (2021.01); *G01L 5/00* (2013.01); *A61B 5/02427* (2013.01)

(56) References Cited

U.S. PATENT DOCUMENTS

| | | | |
|---|---|---|---|
| 2013/0066240 A1* | 3/2013 | Van Heesch | A61N 7/02 601/2 |
| 2014/0330103 A1 | 11/2014 | Yoo | |
| 2017/0251935 A1* | 9/2017 | Yuen | A61B 5/0261 |
| 2017/0255338 A1* | 9/2017 | Medina | G06F 3/0416 |
| 2018/0177413 A1* | 6/2018 | Kwon | A61B 5/022 |

FOREIGN PATENT DOCUMENTS

| | | | | |
|---|---|---|---|---|
| WO | WO-2013099139 A1 * | 7/2013 | | A61B 5/021 |
| WO | 2015/151132 A1 | 10/2015 | | |
| WO | WO-2017053877 A2 * | 3/2017 | | G16H 50/30 |
| WO | WO-2017152098 A1 * | 9/2017 | | A61B 5/6826 |

* cited by examiner

BIO-SIGNAL ACQUIRING APPARATUS, BIO-SIGNAL ACQUIRING METHOD, AND BIO-INFORMATION ESTIMATING METHOD

CROSS-REFERENCE TO RELATED APPLICATION(S)

This application claims priority from Korean Patent Application No. 10-2018-0111200, filed on Sep. 18, 2018, in the Korean Intellectual Property Office, the entire disclosure of which is incorporated herein by reference for all purposes.

BACKGROUND

1. Field

Apparatuses and methods consistent with exemplary embodiments relate to an apparatus and a method for acquiring bio-signals from an object in a non-invasive manner.

2. Description of the Related Art

A method of measuring blood pressure in a non-invasive manner includes a cuff-based measurement method for measuring blood pressure using cuff pressure measurements and a cuffless measurement method for estimating blood pressure using pulse wave measurements without a cuff.

The cuff-based method for measuring blood pressure includes a Korotkoff-sound method which measures blood pressure by winding a cuff around an upper arm and hearing the sound of blood vessels through a stethoscope during inflation and deflation of the cuff; and an Oscillometric method which measures blood pressure by winding a cuff around an upper arm and continuously measuring cuff pressure while inflating and then gradually deflating the cuff using an automated device, and measuring blood pressure based on a point of maximum pressure signal change.

The cuffless measurement method for measuring blood pressure includes a method of estimating blood pressure by calculating a Pulse Transit Time (PTT), and a Pulse Wave Analysis (PWA) method of estimating blood pressure by analyzing a pulse wave form.

SUMMARY

According to an aspect of an exemplary embodiment, there is provided a bio-signal acquiring apparatus, including: a sensor part including a bio-signal sensor, a load sensor, and an ultrasonic sensor array, the bio-signal sensor configured to detect a bio-signal of an object that comes into contact with the sensor part, the load sensor configured to detect a contact load of the object, and the ultrasonic sensor array configured to detect contact load distribution of the object; and a signal processor configured to obtain a contact load of the object at a region of interest based on the contact load and the contact load distribution, and configured to output the contact load of the object at the region of interest and the bio-signal.

The sensor part may have a multi-layer structure, in which the bio-signal sensor is disposed on a top portion, the ultrasonic sensor array disposed below the bio-signal sensor, and the load sensor disposed below the ultrasonic sensor array.

The sensor part may have a multi-layer structure, in which the ultrasonic sensor array is disposed on a top portion, the bio-signal sensor disposed below the ultrasonic sensor array, and the load sensor disposed below the bio-signal sensor.

The ultrasonic sensor array may include a transparent material.

The signal processor may adjust at least one of an amplitude and a frequency of ultrasonic waves of the ultrasonic sensor array.

The sensor part may further include a fingerprint sensor configured to detect fingerprint data of the object.

The signal processor may obtain a contact position of the object based on the fingerprint data, and perform at least one of guiding a contact state of the object based on the contact position and setting the region of interest.

The fingerprint sensor may include a transparent material.

The sensor part may further include a temperature sensor configured to detect temperature of the object.

The signal processor may perform at least one of correcting the bio-signal based on the temperature of the object and guiding a user to re-measure the bio-signal.

The temperature sensor may include a transparent material.

The sensor part may further include: a temperature sensor configured to detect temperature of the object that comes into contact with the temperature sensor, the temperature sensor including a first transparent material; a fingerprint sensor, which is disposed below the temperature sensor and configured to detect fingerprint data of the object, the fingerprint sensor including a second transparent material.

The bio-signal sensor may include one or more of a Photoplethysmogram (PPG) sensor, an Electrocardiography (ECG) sensor, an Electromyography (EMG) sensor, a Seismocardiogram (SCG) sensor, a Ballistocardiogram (BCG) sensor, an Impedance plethysmography (IPG) sensor, a Galvanic Skin Responses (GSR) sensor, and an Impedance sensor.

The signal processor may obtain a contact load at each position of a contact surface by: dividing contact load at a plurality of positions of the contact surface by a total sum of contact load distribution values corresponding to the plurality of positions, to obtain a first value; and multiplying the first value by a contact load distribution value at each position, to obtain the contact load at each position, wherein the signal processor may obtain the contact load of the object at the region of interest based on the contact load at each position.

According to an aspect of another exemplary embodiment, there is provided a bio-signal acquiring apparatus, including: a sensor part including a load sensor configured to detect a contact load of an object that is in contact with the sensor part, and an ultrasonic sensor array configured to detect contact load distribution of the object; and a signal processor configured to obtain a bio-signal of the object based on the contact load distribution, to obtain a contact load of the object at a region of interest based on the contact load and the contact load distribution, and to output the contact load of the object at the region of interest and the bio-signal.

The sensor part may have a multi-layer structure, in which the ultrasonic sensor array is disposed on a top portion, and the load sensor disposed below the ultrasonic sensor array.

The signal processor may adjust at least one of an amplitude and a frequency of ultrasonic waves of the ultrasonic sensor array.

The sensor part may further include at least one of a fingerprint sensor configured to detect fingerprint data of the object, and a temperature sensor configured to detect temperature of the object.

According to an aspect of still another exemplary embodiment, there is provided a bio-signal acquiring method performed by a bio-signal acquiring apparatus, including: detecting a bio-signal, a contact load, and contact load distribution of an object that comes into contact with a sensor part of the bio-signal acquiring apparatus; obtaining a contact load of the object at a region of interest based on the contact load and the contact load distribution; and outputting the contact load of the object at the region of interest and the bio-signal.

The obtaining the contact load of the object at the region of interest includes: dividing contact load at a plurality of positions of a contact surface by a total sum of contact load distribution values corresponding to the plurality of positions, to obtain a first value; multiplying the first value by a contact load distribution value at each position, to obtain the contact load at each position; and obtaining the contact load of the object at the region of interest based on the contact load at each position.

According to an aspect of still another exemplary embodiment, there is provided a bio-information estimating apparatus, including: a bio-signal acquirer configured to detect a bio-signal from an object that comes into contact with a sensor part of the bio-signal acquirer, and detect a contact load and contact load distribution of the object, and to obtain a contact load of the object at a region of interest based on the contact load and the contact load distribution; and a bio-information estimator configured to estimate bio-information based on the bio-signal and the contact load of the object at the region of interest.

BRIEF DESCRIPTION OF THE DRAWINGS

The above and/or other aspects will become apparent and more readily appreciated by describing certain exemplary embodiments with reference to the accompanying drawings, in which.

DETAILED DESCRIPTION

Figure 1:
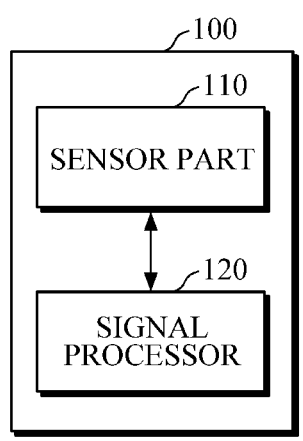
FIG. 1 is a block diagram illustrating an example of a bio-signal acquiring apparatus according to an embodiment.

Details of exemplary embodiments are included in the following detailed description and drawings. Advantages and features of the disclosure, and a method of achieving the same will be more clearly understood from the following embodiments described in detail with reference to the accompanying drawings. Throughout the drawings and the detailed description, unless otherwise described, the same drawing reference numerals will be understood to refer to the same elements, features, and structures.

It will be understood that, although the terms first, second, etc. may be used herein to describe various elements, these elements should not be limited by these terms. These terms are only used to distinguish one element from another. Any references to singular may include plural unless expressly stated otherwise. In addition, unless explicitly described to the contrary, an expression such as "comprising" or "including" will be understood to imply the inclusion of stated elements but not the exclusion of any other elements. Also, the terms, such as 'part' or 'module', etc., should be understood as a unit that performs at least one function or operation and that may be embodied as hardware, software, or a combination thereof. Expressions such as "at least one of," when preceding a list of elements, modify the entire list of elements and do not modify the individual elements of the list. For example, the expression, "at least one of a, b, and c," should be understood as including only a, only b, only c, both a and b, both a and c, both b and c, or all of a, b, and c.

Hereinafter, embodiments of a bio-signal acquiring apparatus and bio-signal acquiring method will be described in detail with reference to the accompanying drawings.

Various embodiments of the bio-signal acquiring apparatus may be embedded in various information processing devices, such as a portable wearable device, a smart device, and the like. Examples of the various information processing devices may include, but are not limited to, a wearable device of various types such as a smart watch worn on the wrist, a smart band-type wearable device, a headphone-type wearable device, a hairband-type wearable device, and the like, a mobile device such as a smartphone, a tablet PC, and the like.

FIG. 1 is a block diagram illustrating an example of a bio-signal acquiring apparatus according to an embodiment. FIGS. 2A to 2F are diagrams explaining structures of a sensor part of the bio-signal acquiring apparatus of FIG. 1. FIG. 3 is a diagram explaining a correlation between a bio-signal and contact load distribution.

Referring to FIG. 1, the bio-signal acquiring apparatus 100 includes a sensor part 110 and a signal processor 120.

The sensor part 110 may detect a bio-signal from an object while the object is in contact with a contact surface. Further, the sensor part 110 may detect a contact load, applied by the object to the contact surface, to measure a bio-signal, and may detect contact load distribution on the contact surface.

While in contact with the contact surface, when the object, e.g., a finger, presses the contact surface with gradually increasing force, a contact load is gradually increased, such that a contact area of the finger becomes wider and contact load distribution also gradually becomes wider. An amplitude of a bio-signal, e.g., a Photoplethysmogram (PPG) signal, changes according to a change in the contact load, i.e., by pressing the contact surface with gradually increasing force, or by gradually decreasing force when the object presses the contact surface with a pressure intensity equal to or greater than a predetermined threshold. In this case, when a contact state of the finger is not appropriate, e.g., in the case where the finger fails to touch an accurate position, or the finger fails to press the contact surface with an appropriate pressure intensity, a bio-signal may be distorted. Further, even when the finger touches an accurate position, the finger generally has a three-dimensional curved surface, such that a contact load acting on the flat sensor part 110 may have different values at each position on the contact surface.

In an embodiment, the sensor part 110 may be configured to detect contact load distribution on the contact surface to measure an actual contact load applied by an object to a specific position, so that bio-information may be accurately estimated regardless of various contact states.

FIGS. 2A to 2F are diagrams illustrating a sensor part 110 implemented in various structures to detect contact load distribution.

Figure 2A:
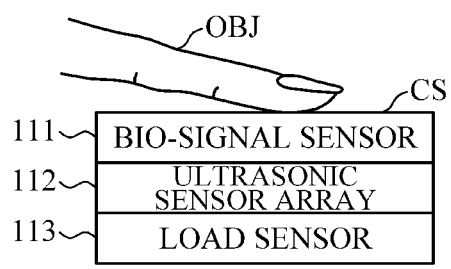
FIGS. 2A to 2F are diagrams explaining structures of a sensor part of the bio-signal acquiring apparatus of FIG. 1.
Figure 2B:
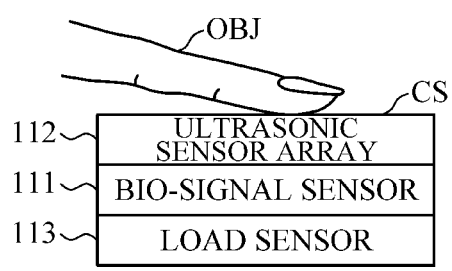
Figure 3:
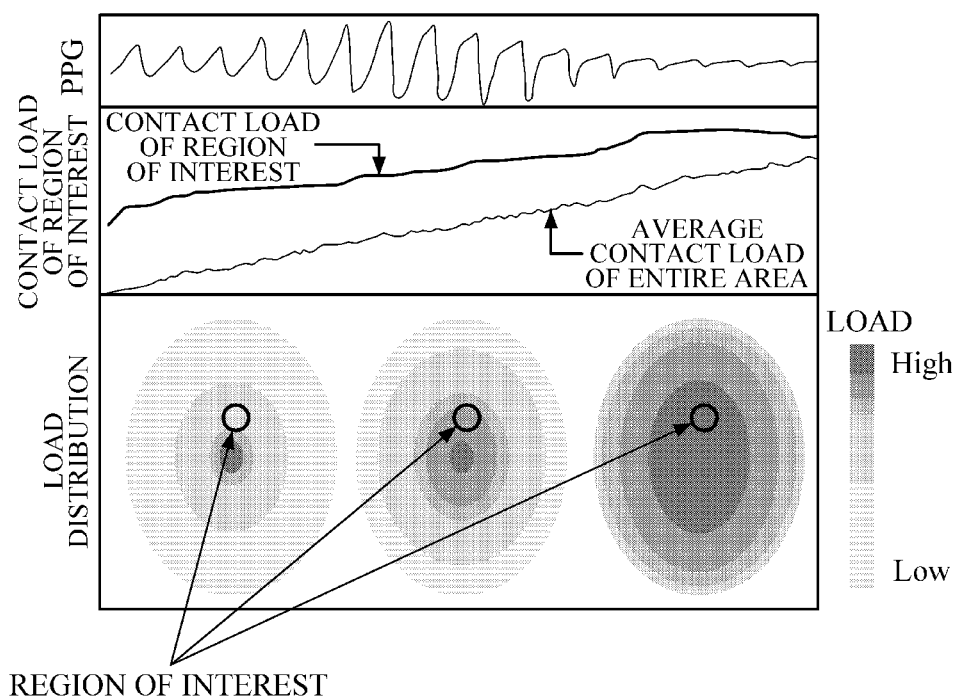
FIG. 3 is a diagram for explaining a correlation between a bio-signal and contact load distribution.

Referring to FIGS. 2A and 2B, the sensor part 110 includes a bio-signal sensor 111, an ultrasonic sensor array 112, and a load sensor 113.

The bio-signal sensor 111 may measure a bio-signal while an object OBJ is in contact with a contact surface CS. The bio-signal sensor 111 may include one or more of a Photoplethysmogram (PPG) sensor, an Electrocardiography (ECG) sensor, an Electromyography (EMG) sensor, a Seismocardiogram (SCG) sensor, a Ballistocardiogram (BCG) sensor, an Impedance plethysmography (IPG) sensor, a Galvanic Skin Responses (GSR) sensor, and an Impedance sensor. The bio-signal sensor 111 may be formed as a sensor or an array of a plurality of sensors by considering distribution of blood vessels of the object OBJ and the like. In the case where the bio-signal sensor 111 is formed as an array of a plurality of sensors, the bio-signal sensor 111 may be formed to correspond to a shape and/or a size of an ultrasonic sensor array 112.

An optical sensor, such as a PPG sensor, includes a light source for emitting light onto the object OBJ, and a detector for detecting light scattered or reflected from the object OBJ. The light source may include a light emitting diode (LED), a laser diode (LD), a fluorescent body, and the like, but is not limited thereto. Further, the detector may include a photo diode, a photo transistor (PTr), an image sensor (e.g., CMOS or CIS image sensor), and the like, but is not limited thereto. The PPG sensor, which includes light source-detector pairs, may be formed as an array having a plurality of PPG sensors arranged in a predetermined shape. In this case, each light source may emit light of different wavelengths.

The ultrasonic sensor array 112 may include a plurality of ultrasonic sensors which are arranged in a two-dimensional N×M matrix having a square shape. However, the ultrasonic sensor array 112 is not limited thereto, and the plurality of ultrasonic sensors may be arranged in a circular shape, an oval shape, and the like, or may be modified in various shapes according to a shape of the object OBJ, and the like. When the object OBJ changes a force applied to the contact surface, each of the ultrasonic sensors may detect a relative size of a contact load at each corresponding position on the contact surface. The ultrasonic waves, generated by the ultrasonic sensor array 112, are reflected when encountering a medium to be detected, in which the amplitude of the reflected ultrasonic waves is changed according to a density of the medium. As the contact load applied by the object OBJ to the contact surface CS increases, a relative density of the object OBJ also increases, thereby affecting the reflected ultrasonic waves. By using such feature, the ultrasonic sensor array 112 may detect a relative size of a contact load at each position.

As described herein, the sensor part 110 may include sensors 111, 112, and 113 which are arranged in a multi-layer structure. For example, as illustrated in FIG. 2A, the bio-signal sensor 111 may be disposed on the top with one surface, on which the contact surface CS is formed to be touched by the object OBJ. The ultrasonic sensor array 112 is disposed below the bio-signal sensor 111, and the load sensor 113 is disposed below the ultrasonic sensor array 112. When the bio-signal sensor 111 is disposed on the top to form the contact surface CS, the bio-signal sensor 111 may directly come into contact with the object OBJ, such that the quality of the measured bio-signal may be improved.

In another example, as illustrated in FIG. 2B, the ultrasonic sensor array 112 is disposed on the top with one surface, on which the contact surface CS is formed. The bio-signal sensor 111 is disposed below the ultrasonic sensor array 112, and the load sensor 113 is disposed below the bio-signal sensor 111. When the ultrasonic sensor array 112 is disposed on the top to form the contact surface CS, contact load distribution based on contact of the object OBJ may be detected accurately. In this case, the ultrasonic sensor array 112 may include a transparent material such as glass, metal, ceramic, polymer, and the like, so as to allow, for example, light emitted by the bio-signal sensor 111 and light scattered or reflected from the object OBJ, to be transmitted without interrupting detection of a bio-signal by the bio-signal sensor 111 disposed below the ultrasonic sensor array 112, but the material of the ultrasonic sensor array 112 is not limited thereto.

Figure 2C:
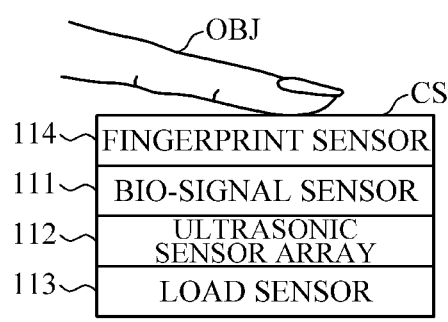

Referring to FIG. 2C, the sensor part 110 may further include a fingerprint sensor 114. The fingerprint sensor 114 may be disposed on the top in the multi-layer structure of each sensor part 110 of FIGS. 2A and 2B. The fingerprint sensor 114 may include one surface, on which the contact surface CS is formed to come into contact with an object OBJ. In this case, the fingerprint sensor 114 may include a transparent material such as glass, metal, ceramic, polymer, and the like, so that light may be transmitted without interrupting detection of a bio-signal by the bio-signal sensor 111 disposed therebelow, but the material of the fingerprint sensor 114 is not limited thereto.

The fingerprint sensor 114 may obtain fingerprint sensor data, such as a contact position, a contact direction, and the like, when the object OBJ comes into contact with the contact surface CS. In this case, the contact position may be a pre-defined feature point, e.g., a center of a fingerprint. The fingerprint sensor 114 may be a capacitive sensor but is not limited thereto. Fingerprint data detected by the fingerprint sensor 114 may be used for determining and guiding a contact state by the signal processor 120, for setting a region of interest and/or for recognizing a user.

Figure 2D:
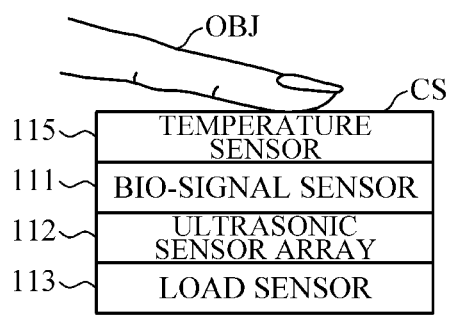

Referring to FIG. 2D, the sensor part 110 may further include a temperature sensor 115. The temperature sensor 115 may be disposed on the top in each structure of the sensor part 110 of FIGS. 2A and 2B. The temperature sensor 115 may have one surface, on which the contact surface CS is formed to come into contact with the object OBJ. In this case, the temperature sensor 115 may include a transparent material such as glass, metal, ceramic, polymer, and the like, so that light may be transmitted without interrupting detection of a bio-signal by the bio-signal sensor 111 disposed below the temperature sensor 115, but the material of the temperature sensor 115 is not limited thereto.

Figure 2E:
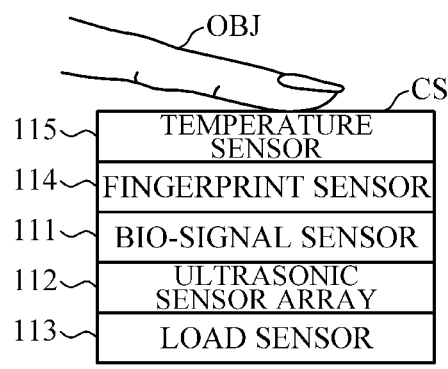

Referring to FIG. 2E, the sensor part 110 may include the temperature sensor 115 which is disposed on the top in the structure of the sensor part 110 of FIG. 2C. In this case, both the temperature sensor 115 and the fingerprint sensor 114 may include a transparent material so that the bio-signal sensor 111 may effectively detect a bio-signal.

The temperature sensor 115 may measure temperature of an object OBJ when the object OBJ comes into contact with the contact surface CS. The temperature of the object OBJ may affect a bio-signal. For example, it is known that there is a correlation between blood pressure and temperature. When bio-information is estimated using a bio-signal, temperature may be measured during measurement of the bio-signal, and bio-information may be estimated accurately by using the measured temperature. The measured temperature may be processed by the signal processor 120, to be used as criteria for correcting a bio-signal and/or determining whether to re-measure a bio-signal, or may be input into a bio-information estimating apparatus to be used for estimating bio-information.

Figure 2F:
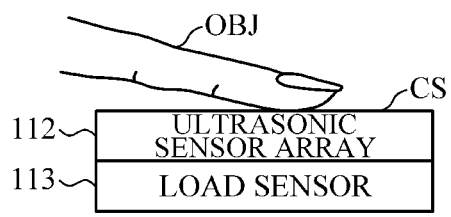

Referring to FIG. 2F, the sensor part 110 may not include the bio-signal sensor 111 in the various structures of the sensor part 110 of FIGS. 2A to 2F. The ultrasonic sensor array 112 may detect a size of a relative contact load at each position of the contact surface CS. Data, detected by the ultrasonic sensor array 112, are processed by the signal processor 120, to be used for acquiring a desired bio-signal, e.g., a signal corresponding to a PPG signal. In this case, as the signal processor 120 may adjust an amplitude and/or a frequency of each ultrasonic sensor of the ultrasonic sensor array 112, a bio-signal may be acquired at different depths within the object OBJ.

The signal processor 120 may be electrically connected to the sensor part 110. The signal processor 120 may perform preprocessing and the like of various signals, such as a bio-signal, a contact load, contact load distribution, temperature data, fingerprint data, and the like, which are electrically converted and output by the sensor part 110. For example, the signal processor 120 may amplify an electric signal output by the sensor part 110, may convert an analog signal into a digital signal, and may perform filtering for noise removal.

Upon receiving a request for acquiring a bio-signal, the signal processor 120 may adjust an amplitude and/or a frequency of each ultrasonic sensor of the ultrasonic sensor array 112. In this case, the amplitude and/or the frequency to be adjusted of the ultrasonic sensor array 112 may be preset for each user according to age, gender, health condition, characteristics of an object and the like, may be set individually for each ultrasonic sensor, or may be set equally for the entire ultrasonic sensor array 112. By adjusting the amplitude and/or the frequency of the ultrasonic sensor array 112, a bio-signal may be acquired at different depths within the contacted object OBJ.

The signal processor 120 may obtain an actual contact load of a region of interest (or contact load applied by the object to the region of interest) based on a contact load and contact load distribution output by the sensor part 110. Further, the signal processor 120 may output an actual contact load of a region of interest to a bio-information estimating apparatus to estimate bio-information.

For example, the signal processor 120 may obtain an actual contact load at each position on the contact surface by using the following Equation 1.

$$P(x, y) = P_r(x, y) \frac{K}{\sum P_r} \quad \text{[Equation 1]}$$

Herein, P(x, y) denotes an actual contact load to be obtained at a position of (x, y) on the contact surface; $P_r$(x, y) denotes a relative size of the contact load at the position of (x, y), i.e., a value corresponding to the position of (x, y) among two-dimensional output values of the ultrasonic sensor array 112; K denotes an output value of the load sensor 113; ΣPr denotes a value obtained by summing all of the relative sizes of the contact load, i.e., a value obtained by summing all of the two-dimensional output values of the ultrasonic sensor array 112.

Upon obtaining the actual contact load at each position on the contact surface, the signal processor 120 may obtain an actual contact load of a region of interest based on actual contact loads at each of the positions included in the region of interest. For example, the signal processor 120 may obtain, as an actual contact load, at least one of a value obtained by summing all of the actual contact loads at each of the positions included in the region of interest, an average value, a maximum value, a minimum value, a median value, other statistical value, and a value calculated by using a pre-defined function.

In one embodiment, a position, a size, a shape, and the like of the region of interest may be pre-defined. For example, the region of interest may be pre-defined to have a predetermined size and/or shape from the center of the contact surface. In another example, the signal processor 120 may dynamically set the region of interest based on a relative size of the contact load detected at each position, an actual contact load obtained at each position, or fingerprint data obtained by the fingerprint sensor 114. For example, the signal processor 120 may set, as the region of interest, a maximum actual contact load point, and a predetermined size and/or a shape from a contact position (e.g., center of a fingerprint) of fingerprint data. Alternatively, the signal processor 120 may set the region of interest by considering distribution of blood vessels of an object, and may set the region of interest based on a point corresponding to a position where the bio-signal sensor 111 in the ultrasonic sensor array 112 is disposed.

The signal processor 120 may output information, regarding the obtained actual contact load of the region of interest and the size of the region of interest, to the bio-information estimating apparatus. The actual contact load and the size of the region of interest may be used by the bio-information estimating apparatus to obtain contact pressure for estimating bio-information.

FIG. 3 is a diagram explaining a correlation between a bio-signal and contact load distribution. Referring to FIG. 3, a bio-signal (e.g., a signal corresponding to a PPG signal) measured for a predetermined period of time is illustrated at the top of the diagram, a change in an average contact load of the entire contact surface and a change in a contact load of the region of interest are illustrated in the middle of the diagram, and a change in contact load distribution of the contact surface for a predetermined period of time is illustrated at the bottom of the diagram. The pressure, applied by a user when the user presses the contact surface with an object, varies depending on age, gender, characteristics of an object, and the like, such that contact pressure may not be measured accurately by using only an average of the entire contact load. In the embodiment, by setting an area, in which a contact state of an object is appropriate, as a region of interest, and by obtaining contact pressure by using an actual contact load of the region of interest, bio-information may be estimated accurately regardless of a contact state.

In addition, the signal processor 120 may determine a contact state based on an actual contact load obtained at each position on the contact surface and/or fingerprint data obtained by the fingerprint sensor 114. For example, the signal processor 120 may compare a value (e.g., an average of an entire surface, an average of a region of interest, a maximum value, a minimum value, etc.), which is calculated based on an actual contact load at each position to determine a contact state, with a predetermined reference value; and in response to the calculated value not satisfying the reference value (or equal to or greater than the reference value), the signal processor 120 may determine that a contact state is failure. In addition, in response to a contact position of fingerprint data, e.g., a fingerprint center, is not within a contact surface, or deviates from the contact surface by more than a predetermined threshold, the signal processor 120 may determine that a contact state is not normal.

Upon determining that the contact state is not normal, the signal processor 120 may control the sensor part 110 to re-measure a bio-signal, or may provide guide information for guiding a user to change a contact position and the like, which are merely exemplary, and the signal processor 120 is not limited thereto.

Once the temperature sensor 116 measures temperature of an object, the signal processor 120 may perform various operations based on temperature information. For example, the signal processor 120 may correct a measured bio-signal according to a reference temperature. In this case, a correction model may be pre-defined according to a difference between the reference temperature and the measured temperature, and the signal processor 120 may correct the bio-signal by applying the correction model. Alternatively, in response to temperature of an object falling outside a reference range, the signal processor 120 may determine that a bio-signal is not accurate, and may control the sensor part 110 to re-measure a bio-signal, or may provide a user with information indicating that the temperature of the object is not within a normal range.

In the case where the bio-signal sensor 111 is not included in the sensor part 110, the signal processor 120 may acquire a signal, corresponding to a bio-signal, based on contact load distribution data detected by the ultrasonic sensor array 112. For example, the signal processor 120 may obtain a statistical value of an actual contact load of entire positions of the contact surface detected by the ultrasonic sensor array 112 at each measurement time point, or a statistical value of an actual contact load of positions included in a region of interest, and may use the obtained statistical value as an amplitude of each measurement time point of a PPG signal. In this case, the statistical value may include a total sum, an average value, a median value, a maximum value, a minimum value, and the like. Alternatively, the signal processor 120 may substitute the obtained statistical value into an amplitude estimation equation, which represents a correlation between the obtained statistical value and an amplitude of a PPG signal, and may obtain a value corresponding to the amplitude of the PPG signal. As can be seen from FIG. 3, the amplitude of the PPG signal is generally increased as the contact load of an object is increased, and the amplitude estimation equation may be defined based on the correlation.

Figure 4:
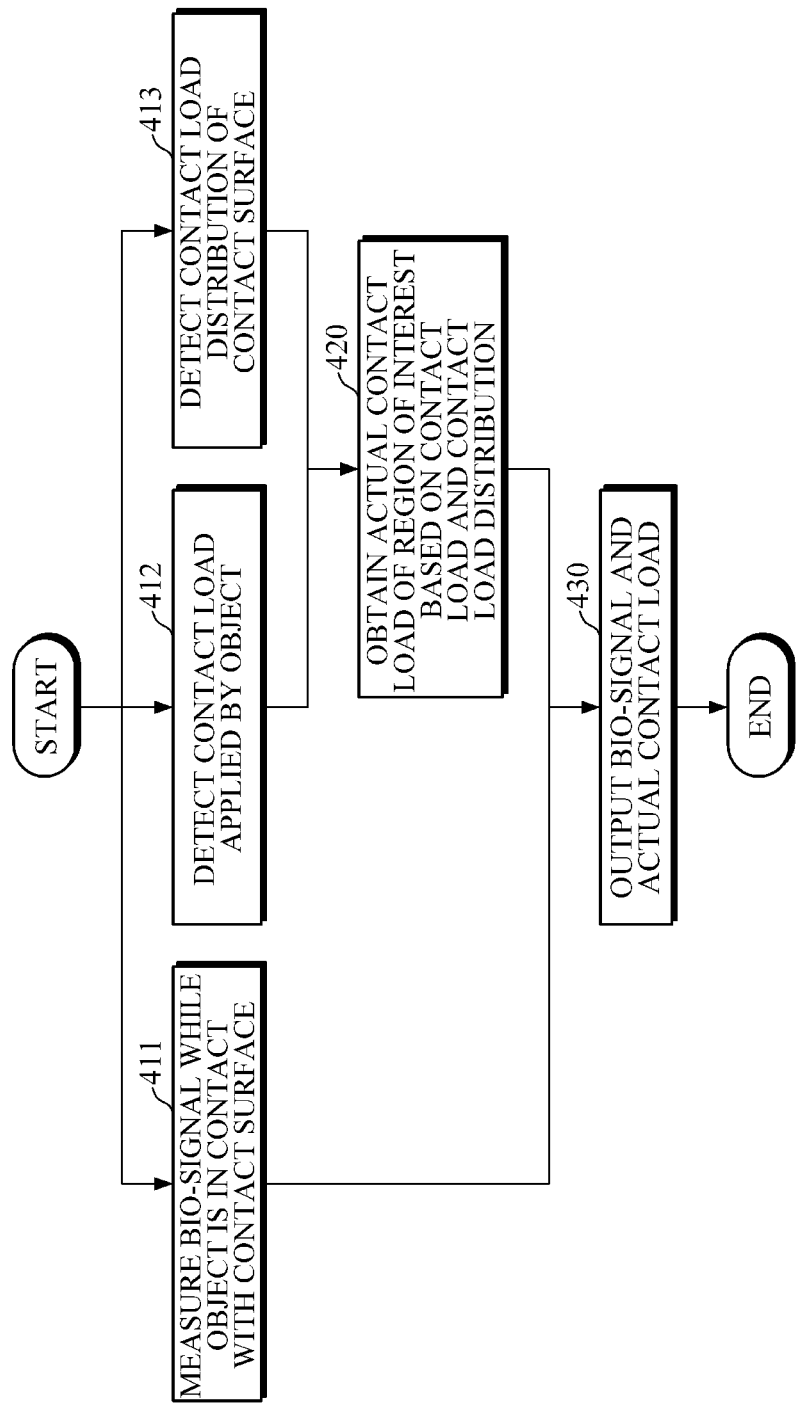
FIG. 4 is a flowchart illustrating a bio-signal acquiring method according to an embodiment.

FIG. 4 is a flowchart illustrating a bio-signal acquiring method according to an embodiment. The bio-signal acquiring method of FIG. 4 is an example of a bio-signal acquiring method performed by the bio-signal acquiring apparatus according to the embodiment of FIG. 1, which is described above in detail such that the method will be briefly described below.

While an object is in contact with the sensor part, the bio-signal acquiring apparatus 100 may detect a bio-signal, a contact load applied by the object, and contact load distribution of a contact surface which comes into contact with the object in 411, 412, and 413. The sensor part of the bio-signal acquiring apparatus 100 may include a bio-signal sensor, an ultrasonic array sensor, and a load sensor, which are formed in a multi-layer structure, to detect the bio-signal, the contact load, and the contact load distribution. The bio-signal sensor or the ultrasonic array sensor may be disposed on the top of the multi-layer structure, and may include a transparent material. In addition, the sensor part may further include a fingerprint sensor, a temperature sensor, an ultrasonic regulator, and the like, which are described above in detail. In the case where the bio-signal sensor is not included, the bio-signal may be acquired based on contact load distribution detected by the ultrasonic sensor array.

The bio-signal acquiring apparatus 100 may obtain an actual contact load of a region of interest by using the detected contact load and contact load distribution in 420. The contact load distribution data, detected by the ultrasonic sensor array, may include a relative size of a contact load at each position, and the bio-signal acquiring apparatus 100 may obtain the actual contact load at each position by using the contact load and the relative size thereof at each position. Further, the region of interest may be preset according to various criteria, or may be set dynamically using the contact load distribution, fingerprint data, and the like.

Subsequently, the bio-signal acquiring apparatus 100 may output the bio-signal and the actual contact load in 430. The information output by the bio-signal acquiring apparatus 100 may be transmitted to a bio-information estimating apparatus or may be visually provided to a user through a display.

Figure 5:
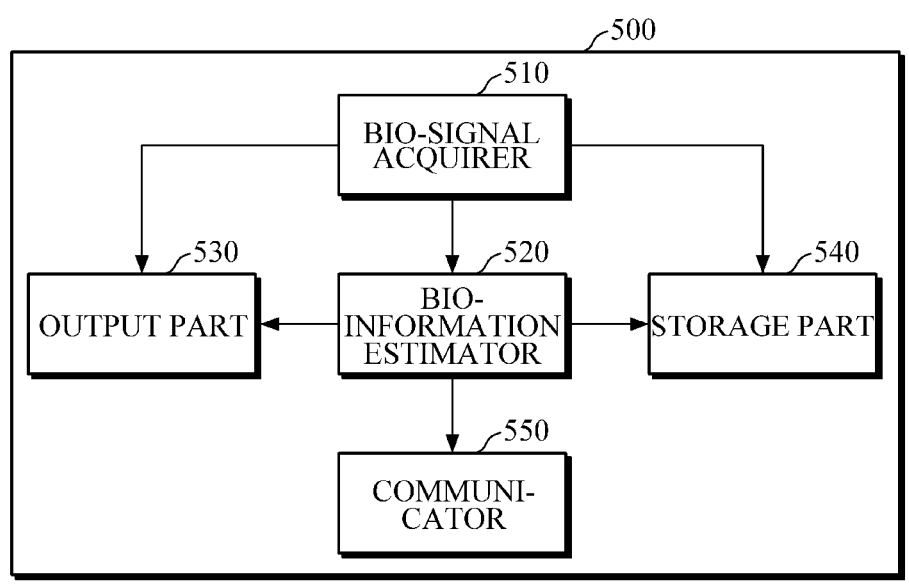
FIG. 5 is a block diagram illustrating a bio-information estimating apparatus according to an embodiment.
Figure 6A:
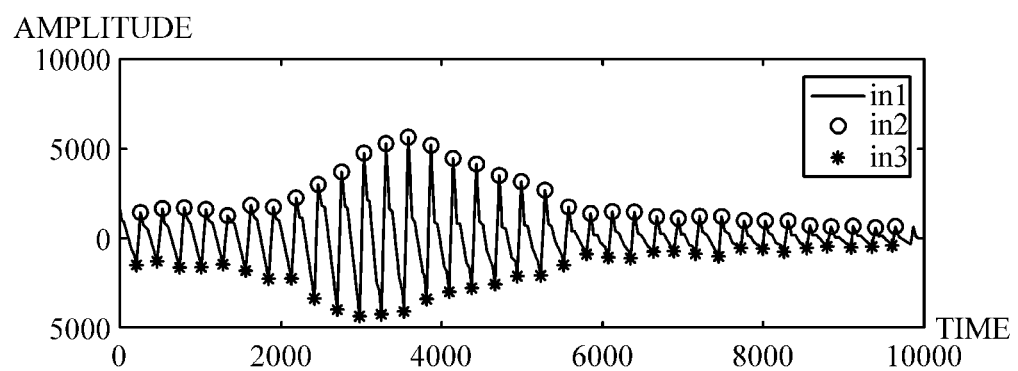
FIGS. 6A and 6B are diagrams for explaining an example of estimating blood pressure.
Figure 6B:
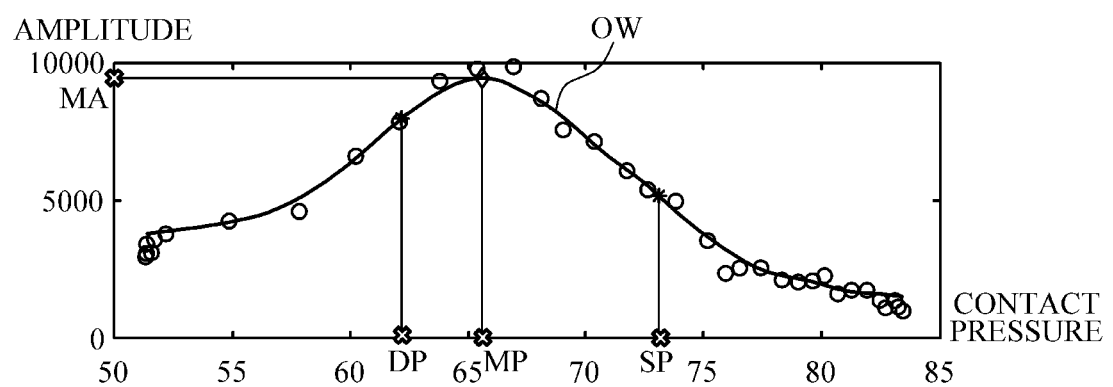

FIG. 5 is a block diagram illustrating a bio-information estimating apparatus according to an embodiment. FIGS. 6A and 6B are diagrams for explaining an example of estimating blood pressure.

Referring to FIG. 5, the bio-information estimating apparatus 500 includes a bio-signal acquirer 510, a bio-information estimator 520, an output part 530, a storage part 540, and a communicator 550.

The bio-signal acquirer 510 may be an example of the aforementioned bio-signal acquiring apparatus 100 or a modified example thereof. The bio-signal acquirer 510 includes the sensor part having the aforementioned structures and the signal processor. Various embodiments of the bio-signal acquirer 510 are described above, such that detailed description thereof will be omitted. At least some of the functions of the bio-signal acquirer 510, which are described above, may be integrated into other parts 520, 530, 540, and 550. Further, the function of the signal processor of the bio-signal acquirer 510 and the bio-information estimator 520 may be integrated into one processor or may be individually implemented as two or more processors.

The bio-information estimator 520 may estimate bio-information based on a bio-signal output by the bio-signal acquirer 510 and an actual contact load of a region of interest. For example, the bio-information estimator 520 may obtain contact pressure by dividing the actual contact load of a region of interest by an area of the region of interest. In this case, the area of the region of interest may be identified according to a setting of the region of interest.

Upon obtaining contact pressure, the bio-information estimator 520 may obtain an oscillometric envelope by using the obtained contact pressure and the bio-signal, e.g., the pulse wave signal, and may extract feature values for estimating blood pressure from the oscillometric envelope, to estimate blood pressure based on oscillometry.

FIGS. 6A and 6B are diagrams for explaining a method of estimating blood pressure based on oscillometry using contact pressure and a pulse wave signal. Referring to FIG. 6A, the bio-information estimator 520 may extract a peak-to-peak point by subtracting an amplitude value in3 of a negative (−) point from an amplitude value in2 of a positive (+) point of the waveform envelope in1 at each measurement time point of a pulse wave signal. Referring to FIG. 6B, the bio-information estimator 520 may obtain an oscillometric envelope OW by plotting a peak-to-peak amplitude at each measurement time point based on a contact pressure value at the same measurement time point as the peak-to-peak amplitude. The bio-information estimator 520 may obtain one or more feature values from the obtained oscillometric envelope OW. Referring to FIG. 6B, the bio-information estimator 520 may obtain, as the feature value, an amplitude value MA and a contact pressure value MP of a maximum peak point, contact pressure values SP and DP located to the left and right of the contact pressure value MP of the maximum peak point and having a predetermined ratio (e.g., 0.5 to 0.7) to the contact pressure value MP, and the like.

The bio-information estimator 520 may estimate bio-information by combining the extracted feature values by using a pre-defined bio-information estimation model. In this case, the bio-information estimation model may be defined as various linear or non-linear combination functions, such as addition, subtraction, division, multiplication, logarithmic value, regression equation, and the like, with no specific limitation. For example, the following Equation 2 represents a simple linear equation.

$$y=ax+b \qquad \text{[Equation 2]}$$

Herein, y denotes bio-information to be obtained; x denotes the extracted feature value; and a and b denote pre-calculated values obtained through preprocessing, and may be defined differently according to the types of bio-information to be obtained and user characteristics. For example, the bio-information estimator 230 may independently obtain mean arterial pressure (MAP), diastolic blood pressure (DBP), and systolic blood pressure (SBP) by using the above Equation 2 which is defined for each of the MAP, the DBP, and the SBP. For example, the bio-information estimator 520 may obtain the MAP, the DBP, and the SBP by substituting the extracted feature values MP, DP, and SP into a function defined for each of the values.

The output part 530 may output results processed by the bio-signal acquirer 510 and the bio-information estimator 520. For example, the output part 530 may visually output an estimated bio-information value and/or guide information on a contact state by using a display module (e.g., display device), or may output the information in a non-visual manner through voice, vibration, tactile sensation, and the like, by using a speaker module, a haptic module, and the like. In this case, if an estimated bio-information value falls outside a normal range, the output part 530 may output warning information in various manners, such as highlighting an abnormal value in red and the like, displaying the abnormal value along with a normal range, outputting a voice warning message, adjusting a vibration intensity, and the like.

The storage part 540 may store results processed by the bio-signal acquirer 510 and the bio-information estimator 520. Further, the storage part 540 may store various types of reference information required for estimating bio-information. For example, the reference information may include user feature information such as a user's age, gender, occupation, health condition, and the like. In addition, the reference information may include various types of information, such as a bio-information estimation model, bio-information estimation criteria, a reference temperature range, a correction model, and the like, but is not limited thereto.

In this case, the storage part 540 may include at least one storage medium of a flash memory type memory, a hard disk type memory, a multimedia card micro type memory, a card type memory (e.g., an SD memory, an XD memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, and an optical disk, and the like, but is not limited thereto.

The communicator 550 may communicate with an external device by using wired or wireless communication techniques, and may transmit and receive various data to and from the external device. For example, the communicator 550 may transmit an estimation result of bio-information to the external device, and may receive various types of reference information required for estimating bio-information from the external device. In this case, examples of the external device may include a cuff-type blood pressure measuring device, and an information processing device such as a smartphone, a tablet PC, a desktop computer, a laptop computer, and the like.

In this case, examples of the communication techniques may include Bluetooth communication, Bluetooth Low Energy (BLE) communication, Near Field Communication (NFC), WLAN communication, Zigbee communication, Infrared Data Association (IrDA) communication, Wi-Fi Direct (WFD) communication, Ultra-Wideband (UWB) communication, Ant+communication, WIFI communication, Radio Frequency Identification (RFID) communication, 3G communication, 4G communication, 5G communication, and the like. However, this is merely exemplary and is not intended to be limiting.

Figure 7:
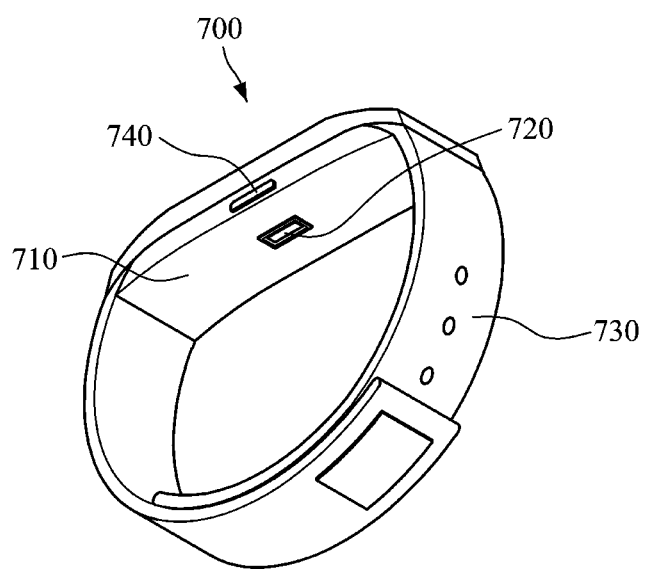
FIG. 7 is a diagram illustrating a wearable device, to which a bio-information estimating apparatus is applied.

FIG. 7 is a diagram illustrating a wearable device, to which embodiments of a bio-information estimating apparatus are applied. Various embodiments of the above-described bio-information estimating apparatus 500 may be mounted in a smart watch worn on a wrist or a smart band-type wearable device as illustrated herein. However, the wearable device is merely an example for convenience of explanation, and it should not be construed that application of the embodiments is limited to a smart watch or a smart band-type wearable device.

Referring to FIG. 7, the wearable device 700 includes a main body 710 and a strap 730.

The strap 730 may be flexible, and may be connected to both ends of the main body 710 to be bent around a user's wrist or may be bent in a manner which allows the strap 730 to be detached from a user's wrist. Alternatively, the strap 730 may be formed as a band that is not detachable. In this case, air may be injected into the strap 730 or an airbag may be included in the strap 730, so that the strap 730 may have elasticity according to a change in pressure applied to the wrist, and the change in pressure of the wrist may be transmitted to the main body 710.

A battery, which supplies power to the wearable device 700, may be embedded in the main body 710 or the strap 730.

Further, the main body 710 includes, on one side, a sensor part 720. The sensor part 720 comes into contact with the wrist to measure a bio-signal, a contact load, and contact load distribution from blood vessel tissues of the wrist. As described above, the sensor part 720 may have various multi-layer structures. When a user changes a contact intensity between the wrist and the sensor part 720 for a predetermined period of time to estimate bio-information, the sensor part 720 may measure the bio-signal, the contact load, and the contact load distribution.

For example, a user may change contact pressure between the wrist and the sensor part 720 while wearing the main body 710 by touching a display, mounted on one surface of the main body 710, with gradually increasing force with a finger of the other hand. Alternatively, a user may change a thickness of the wrist by making hand movements, e.g., slowly opening the hand after clenching the first while wearing the main body 710 on the wrist. In this case, the change in the thickness of the wrist leads to a change hi tension of the strap wrapped around the wrist, thereby causing a change in contact pressurebetween the wrist and the sensor part 720.

Further, the main body 710 may include a processor which processes information on the bio-signal, the contact load, the contact load distribution, and the like, which are detected by the sensor part 720, and estimates bio-information by using the processing results. Upon receiving a request for estimating bio-information from a user, the processor may generate a control signal to control the sensor part 720. Once the sensor part 720 detects the contact load and the contact load distribution, the processor may obtain an actual contact load of a region of interest, and may estimate bio-information by using the actual contact load of the region of interest and the bio-signal. For example, the processor may calculate a contact pressure value based on the actual contact load and the area of the region of interest, and may estimate blood pressure based on oscillometry using the calculated contact pressure value and the pulse wave signal.

Upon receiving the request for estimating bio-information from a user, the processor may provide the user with guide information on a contact state through a display, the user may apply pressure to the main body 710 to change the contact press between the sensor part 720 and the object. In this case, the display may be mounted on a front surface of the main body 710, and may visually output guide information on a contact state and/or an estimation result of bio-information.

The storage part may be mounted body 710, and ma types of information processed by the processor, and various criteria for estimating information.

Further, the wearable device 700 may include a manipulator 740 which receives a control command of a user and transmits the received control command to the processor. The manipulator 740 may be mounted on a side surface of the main body 710, and may include a function for inputting a command to turn on/off the wearable device 700.

Moreover, the wearable device 700 may include a communicator for transmitting and receiving various data to and from an external device, and various other modules for performing additional functions provided by the wearable device 700.

Figure 8:
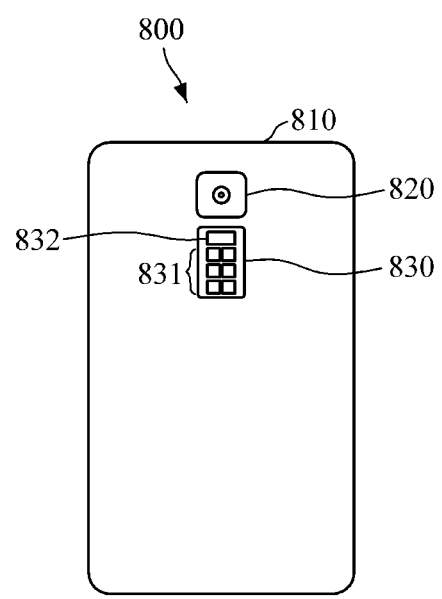
FIG. 8 is a diagram illustrating a smart device, to which a bio-information estimating apparatus is applied.

FIG. 8 is a diagram illustrating a smart device, to which embodiments of a bio-information estimating apparatus are applied. In this case, the smart device may be a smartphone, a tablet PC, and the like.

Referring to FIG. 8, the smart device 800 includes a sensor part 830 mounted on one surface of a main body 810. In this case, the sensor part 830 may have a multi-layer structure, including a pulse wave sensor which includes at least one or more light sources 831 and a detector 832, an ultrasonic sensor array which detects contact load distribution, and a load sensor which detects contact load. However, the sensor part 830 is not limited thereto, and may further include a fingerprint sensor, a temperature sensor and/or an ultrasonic regulator, as described above.

The sensor part 830 may be mounted on a rear surface of the main body 810, but is not limited thereto. Further, the sensor part 830 may be configured in combination with a fingerprint sensor or a touch panel mounted on a front surface.

In addition, a display may be mounted on a front surface of the main body 810. The display may visually display an estimation result of bio-information and the like. The display may include a touch panel, and may receive various types of information input through the touch panel and transmit the received information to the processor.

Moreover, an image sensor 820 may be mounted in the main body 810. When a user's fin aches the sensor part 830 to measure a pulse wave signal, the image sensor 820 may capture an image of the finger and may transmit the captured image to the processor. In this case, based on the image of the finger, the processor may identify a relative position of the finger with respect to an actual position of the sensor part 830, and may provide the relative position the finger to the user through the display, so that pulse wave signals may be measured with improved accuracy.

Various other modules for performing many embodiments of the aforementioned bio-information estimating apparatus may be mounted in the smart device 800, and detailed description thereof will be omitted.

The disclosure can be realized as a computer-readable code written on a computer-readable recording medium. The computer-readable recording medium may be any type of recording device which data is stored in a computer-readable manner.

Examples of the computer-readable recording medium include a ROM, a RAM, a CD-ROM, a magnetic tape, a floppy disc, an optical data storage, and a carrier wave (e.g., data transmission through the Internet). The computer-readable recording mediums can be distributed over a plurality of computer systems connected to a network so that a computer-readable code is written thereto and executed there decentralized manner. Functional programs, codes, and code segments needed for realizing the disclosure can be easily deduced by one of ordinary skill in the art.

At least one of the components, elements, modules or units described herein may be embodied as various numbers of hardware, software and/or firmware structures that execute respective functions described above, according to an exemplary embodiment. For example, at least one of these components, elements or units may use a direct circuit structure, such as a memory, a processor, a logic circuit, a look-up table, etc. that may execute the respective functions through controls of one or more microprocessors or other control apparatuses. Also, at least one of these components, elements or units may be specifically embodied by a module, a program, or a part of code, which contains one or more executable instructions for performing specified logic functions, and executed by one or more microprocessors or other control apparatuses. Also, at least one of these components, elements or units may further include or implemented by a processor such as a central processing unit (CPU) that performs the respective functions, a microprocessor, or the like. Two or more of these components, elements or units may be combined into one single component, element or unit which performs all operations or functions of the combined two or more components, elements of units. Also, at least part of functions of at least one of these components, elements or units may be performed by another of these components, element or units. Further, although a bus is not illustrated in some of block diagrams, communication between the components, elements or units may be performed through the bus. Functional aspects of the above exemplary embodiments may be implemented in algorithms that execute on one or more processors. Furthermore, the components, elements or units represented by a block or processing operations may employ any number of related art techniques for electronics configuration, signal processing and/or control, data processing and the like.

The disclosure has been described herein with regard to exemplary embodiments. However, it will be obvious to those skilled in the art that various changes and modifications can be made without changing technical conception and essential features of the disclosure. Thus, it is clear that the above-described embodiments are illustrative in all aspects and are not intended to limit the disclosure.

What is claimed is:

1. A bio-signal acquiring apparatus, comprising:
a sensor part comprising a bio-signal sensor, a load sensor, and an ultrasonic sensor array, the bio-signal sensor configured to detect a bio-signal of an object that comes into contact with the sensor part, the load sensor configured to detect a contact load of the object, and the ultrasonic sensor array configured to detect a contact load distribution of the object, the contact load distribution indicating a relative size of a contact load at each position of a contact surface, which is represented by a two-dimensional output value of the ultrasonic sensor array corresponding to each position of the contact surface; and
a signal processor configured to obtain a contact load of the object at a region of interest based on the contact load and the contact load distribution, and configured to output the contact load of the object at the region of interest and the bio-signal,
wherein the signal processor is further configured to obtain an actual contact load at each position of the contact surface by:
dividing the contact load of the object detected by the load sensor with a total sum of two-dimensional output values of the ultrasonic sensor array at a plurality of positions of the contact surface, to obtain a first value; and
multiplying the first value by the relative size of the contact load at each position, to obtain the actual contact load at each position, and
wherein the signal processor is further configured to obtain the contact load of the object at the region of interest based on the actual contact load at each position.

2. The apparatus of claim 1, wherein the sensor part has a multi-layer structure, in which the bio-signal sensor is disposed on a top portion, the ultrasonic sensor array disposed below the bio-signal sensor, and the load sensor disposed below the ultrasonic sensor array.

3. The apparatus of claim 1, wherein the sensor part has a multi-layer structure, in which the ultrasonic sensor array is disposed on a top portion, the bio-signal sensor disposed below the ultrasonic sensor array, and the load sensor disposed below the bio-signal sensor.

4. The apparatus of claim 3, wherein the ultrasonic sensor array comprises a transparent material.

5. The apparatus of claim 1, wherein the signal processor is further configured to adjust at least one of an amplitude and a frequency of ultrasonic waves of the ultrasonic sensor array.

6. The apparatus of claim 1, wherein the sensor part further comprises a fingerprint sensor configured to detect fingerprint data of the object.

7. The apparatus of claim 6, wherein the signal processor is further configured to obtain a contact position of the object based on the fingerprint data, and perform at least one of guiding a contact state of the object based on the contact position and setting the region of interest.

8. The apparatus of claim 6, wherein the fingerprint sensor comprises a transparent material.

9. The apparatus of claim 1, wherein the sensor part further comprises a temperature sensor configured to detect temperature of the object.

10. The apparatus of claim 9, wherein the signal processor is configured to perform at least one of correcting the bio-signal based on the temperature of the object and guiding a user to re-measure the bio-signal.

11. The apparatus of claim 9, wherein the temperature sensor comprises a transparent material.

12. The apparatus of claim 1, wherein the sensor part further comprises:
a temperature sensor configured to detect temperature of the object that comes into contact with the temperature sensor, the temperature sensor comprising a first transparent material; and
a fingerprint sensor, which is disposed below the temperature sensor and configured to detect fingerprint data of the object, the fingerprint sensor comprising a second transparent material.

13. The apparatus of claim 1, wherein the bio-signal sensor comprises one or more of a Photoplethysmogram (PPG) sensor, an Electrocardiography (ECG) sensor, an Electromyography (EMG) sensor, a Seismocardiogram (SCG) sensor, a Ballistocardiogram (BCG) sensor, an Impedance plethysmography (IPG) sensor, a Galvanic Skin Responses (GSR) sensor, and an Impedance sensor.

14. A bio-signal acquiring apparatus, comprising:
a sensor part comprising a load sensor configured to detect a contact load of an object that is in contact with the sensor part, and an ultrasonic sensor array configured to detect a contact load distribution of the object, the contact load distribution indicating a relative size of a contact load at each position of a contact surface, which is represented by a two-dimensional output value of the ultrasonic sensor array corresponding to each position of the contact surface; and
a signal processor configured to obtain a bio-signal of the object based on the contact load distribution, to obtain a contact load of the object at a region of interest based on the contact load and the contact load distribution, and to output the contact load of the object at the region of interest and the bio-signal,
wherein the signal processor is further configured to obtain an actual contact load at each position of the contact surface by:
dividing the contact load of the object detected by the load sensor with a total sum of two-dimensional output values of the ultrasonic sensor array at a plurality of positions of the contact surface, to obtain a first value; and
multiplying the first value by the relative size of the contact load at each position, to obtain the actual contact load at each position, and
wherein the signal processor is further configured to obtain the contact load of the object at the region of interest based on the actual contact load at each position.

15. The apparatus of claim 14, wherein the sensor part has a multi-layer structure, in which the ultrasonic sensor array is disposed on a top portion, and the load sensor disposed below the ultrasonic sensor array.

16. The apparatus of claim 14, wherein the signal processor is configured to adjust at least one of an amplitude and a frequency of ultrasonic waves of the ultrasonic sensor array.

17. The apparatus of claim 14, wherein the sensor part further comprises at least one of a fingerprint sensor configured to detect fingerprint data of the object, and a temperature sensor configured to detect temperature of the object.

18. A bio-signal acquiring method performed by a bio-signal acquiring apparatus, comprising:
- detecting a bio-signal, a contact load, and a contact load distribution of an object that comes into contact with a sensor part of the bio-signal acquiring apparatus;
- obtaining a contact load of the object at a region of interest based on the contact load and the contact load distribution; and
- outputting the contact load of the object at the region of interest and the bio-signal,
- wherein the detecting comprises detecting the contact load by using a load sensor, and detecting the contact load distribution by using a ultrasonic sensor array, the contact load distribution indicating a relative size of a contact load at each position of a contact surface, the respective size being represented by a two-dimensional output value of the ultrasonic sensor array corresponding to each position of the contact surface,
- wherein the obtaining comprises:
  - dividing the contact load of the object detected by the load sensor with a total sum of two-dimensional output values of the ultrasonic sensor array at a plurality of positions of the contact surface, to obtain a first value;
  - multiplying the first value by the relative size of the contact load at each position, to obtain an actual contact load at each position; and
  - obtaining the contact load of the object at the region of interest based on the actual contact load at each position.

19. A bio-information estimating apparatus, comprising:
- a bio-signal acquirer configured to detect a bio-signal from an object that comes into contact with a sensor part of the bio-signal acquirer, and detect a contact load by using a load sensor and detect a contact load distribution of the object by using a ultrasonic sensor array, and to obtain a contact load of the object at a region of interest based on the contact load and the contact load distribution; and
- a bio-information estimator configured to estimate bio-information based on the bio-signal and the contact load of the object at the region of interest,
- wherein the contact load distribution indicates a relative size of a contact load at each position of a contact surface, the respective size being represented by a two-dimensional output value of the ultrasonic sensor array corresponding to each position of the contact surface,
- wherein the bio-signal acquirer is further configured to obtain an actual contact load at each position of the contact surface by:
  - dividing the contact load of the object detected by the load sensor with a total sum of two-dimensional output values of the ultrasonic sensor array at a plurality of positions of the contact surface, to obtain a first value; and
  - multiplying the first value by the relative size of the contact load at each position, to obtain the actual contact load at each position, and
- wherein the bio-signal acquirer is further configured to obtain the contact load of the object at the region of interest based on the actual contact load at each position.

* * * * *